(12) United States Patent
Wang et al.

(10) Patent No.: US 8,217,013 B2
(45) Date of Patent: Jul. 10, 2012

(54) POLYENE DIESTER ANTIBIOTICS

(75) Inventors: Wenmei Wang, Shanghai (CN); Wang Shuhui, Shanghai (CN); Li Ji'an, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 90 days.

(21) Appl. No.: 12/671,024

(22) PCT Filed: Jul. 30, 2007

(86) PCT No.: PCT/CN2007/070382
§ 371 (c)(1),
(2), (4) Date: Jan. 27, 2010

(87) PCT Pub. No.: WO2009/015541
PCT Pub. Date: Feb. 5, 2009

(65) Prior Publication Data
US 2010/0210576 A1    Aug. 19, 2010

(51) Int. Cl.
*A61K 31/70* (2006.01)
*C07H 17/08* (2006.01)
(52) U.S. Cl. .......................................... 514/31; 536/6.5
(58) Field of Classification Search .................... 536/6.5
See application file for complete search history.

(56) References Cited

U.S. PATENT DOCUMENTS
5,981,721 A    11/1999    Mohan

FOREIGN PATENT DOCUMENTS
| CN | 101081860 | 12/2007 |
| WO | WO 01/51061 | 7/2001 |
| WO | WO 01/91758 | 12/2001 |

OTHER PUBLICATIONS

Pontani, D.R., et al., Anti-Viral and Immunoenhancing Activity of the Methyl Ester of Amphotericin, FASEB J, Mar. 15, 1988, 2(4), Abs 3105.
Racis, S., et al., Protection of Cells Against AIDS Virus by Amphotericin B Methyl Ester, Mar. 15, 1988, 2(4), Abs 3598.
International Search Report for PCT/CN2007/070382, May 15, 2008, Shanghai Institute of Pharmaceuticals Industry, et al.

*Primary Examiner* — Elli Peselev
(74) *Attorney, Agent, or Firm* — Syndicated Law; Brian S. Boyer

(57) ABSTRACT

The present invention discloses a new polyene diester and its preparation. This polyene diester has a structure of Formula 1, which is used as prodrugs by introducing diester group to polyene antibiotics, and these prodrugs exhibit antifungal or antiviral activities through releasing parent polyenes by esterase in vivo. The new derivatives have good antimicrobial activity and better safety. These new derivatives are useful for the antifungal and antiviral treatment. PA-COOR Formula 1

11 Claims, 3 Drawing Sheets

POLYENE DIESTER ANTIBIOTICS

CROSS-REFERENCE TO RELATED APPLICATIONS

This application is a National Stage of International Application No. PCT/CN2007/070382, filed Jul. 30, 2007, which is hereby incorporated herein by reference in its entirety.

TECHNICAL FIELD

This invention relates to pharmaceutical synthesis field, and more particularly, relates to the synthesis of antifungal drugs.

TECHNICAL BACKGROUND

The research and development of antifungal drugs is one of the important areas of antibiotic drugs, and is also one of the areas which have always been drawing the attention of pharmaceutical researchers. With the development of the times, especially with the development of organ transplantation, and the fast propagation of AIDS, the fungal infection is also significantly increased, and particularly, the incidence of deep fungal infection is also increased remarkably, showing a tendency of continuing increasing. Therefore, it has clinical significance to control deep fungal infection effectively. Drugs for the treatment of fungal infection include polyene antibiotics produced by microorganism, for example, amphotericin B, mycostatin, etc., and synthetic drugs including bifonazole, butenafine, ketoconazole, miconazole, sertaconazole, fluconazole, etc. However, in the treatment of deep fungal infection diseases, the most effective product is still amphotericin B which almost has antifungal activity for all fungal, and the minimum inhibitory concentration (MIC) for most of the fungal is 0.02-1 μg/ml. However, amphotericin B has high toxicity, and its therapeutic dose and toxic dose are very close, which brings unsafety to the deep fungal infection patients.

In the nineties, amphotericin B liposome was first developed in Ireland, which can increase its plasma concentration and prolong its half-life to increase the administration safety; however, its preparation conditions are very strict, the emulsion particles must be extremely fine and the requirements for the equipment are very high. The research report from overseas regarding amphotericin B derivatives also includes the preparation of its salts, amides, esters, etc.

The ester derivatives, including its methyl ester, ethyl ester and acryl ester, have been reported, however, there is no report regarding its diester derivatives. Its methyl ester derivative was studied by Rutgers University, New Jersey, US, whose purpose was aiming at HIV infection. It was found that the toxicity was lowered, and it may become anti-HIV drug. However, till now, there is no further report. The amphotericin methyl ester reported by Rutgers University has to be hydrolyzed under alkaline condition by Chemical methods, and it cannot be hydrolyzed by esterase in vivo.

It is necessary to provide a new polyene ester derivative suitable for antibiotic, which can be hydrolyzed by esterase in vivo, with mild conditions, not easy to be destroyed, therefore to achieve the purpose of good effect and low toxicity.

SUMMARY OF THE INVENTION

The object of this invention is to provide a kind of polyene diester compound.

Another object of this invention is to provide a method for preparing this compound.

Still another object of this invention is to provide a pharmaceutical composition containing this compound.

Still another object of this invention is to provide use of this compound.

On one aspect of this invention, the invention provides a polyene diester compound represented by Formula 1 or pharmaceutically acceptable salt thereof:

$$PA\text{-}COOR \qquad \text{Formula 1}$$

wherein, PA is selected from the following polyene antibiotic nuclear parent:

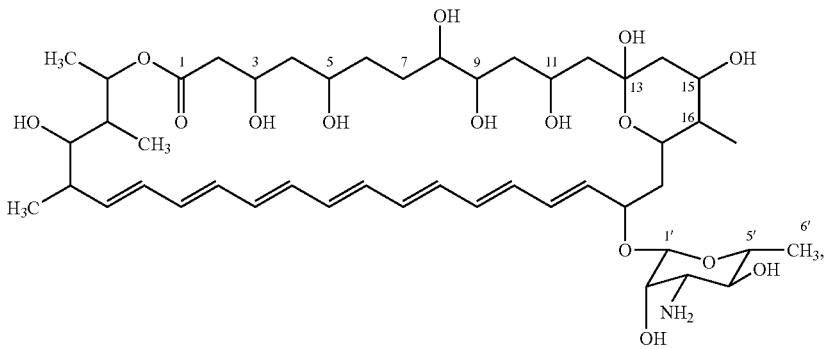

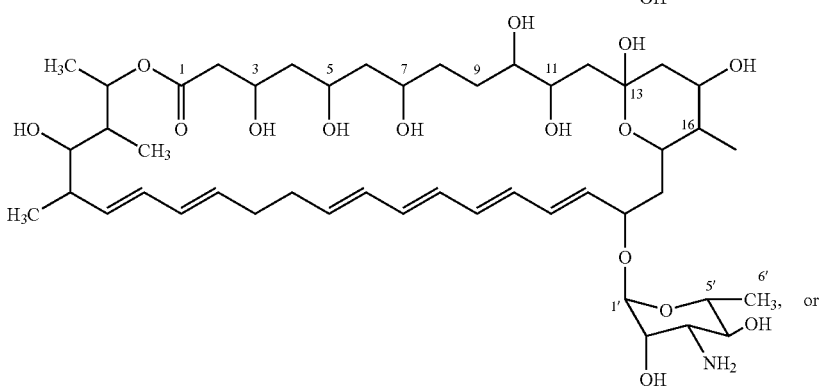

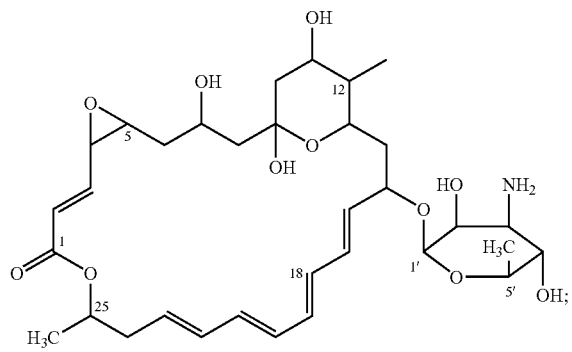
R is a linear or cyclic carbonate or carboxylic acid ester group.
In other preferred embodiment, said PA has the following stereostructure:
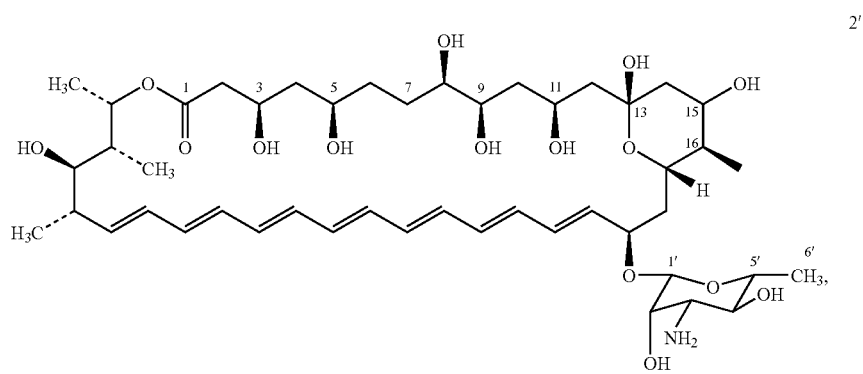
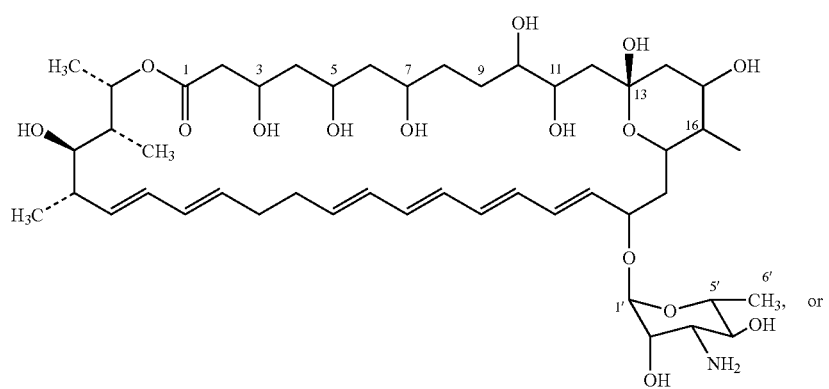
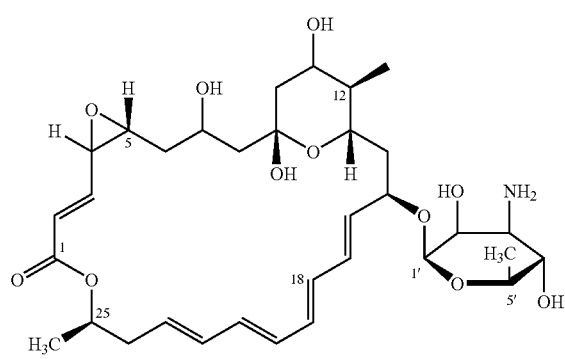

In another preferred embodiment, R is a group containing 2-15 carbon atoms and having 1-3 liner or cyclic carbonate or carboxylic acid ester groups.

In another preferred embodiment, said R contains 2-10 carbon atoms.

In another preferred embodiment, R is selected from:

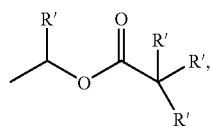  18

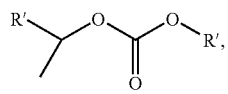  19

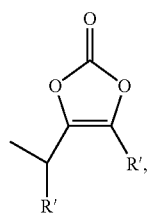  20

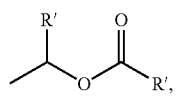  21

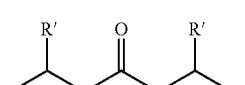  22

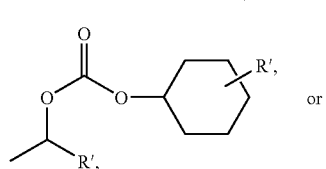  or  23

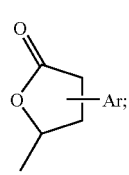  11 wherein, R' is selected from halogen, C1-C3 alkyl or hydroxyl;

Ar is selected from aryl, hetero aromatic ring's containing nitrogen, sulphur, oxygen, or substituted aryl or hetero aromatic rings containing nitrogen, sulphur, oxygen, with 1-3 substituents selected from halogen, C1-C3 alkyl, amino or hydroxyl.

In another preferred embodiment, R is selected from:

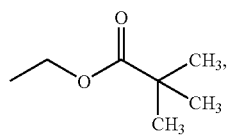  5

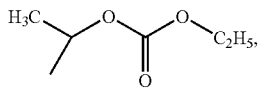  6

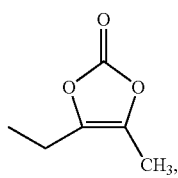  7

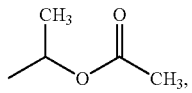  8

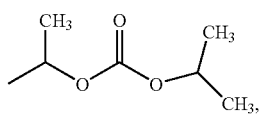  9

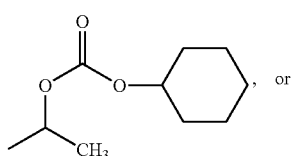  , or  10

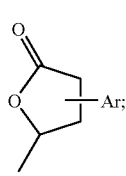  11 wherein, Ar is selected from aryl, hetero aromatic rings containing nitrogen, sulphur, oxygen, or substituted aryl or hetero aromatic rings containing nitrogen, sulphur, oxygen, with 1-3 substituents selected from halogen, C1-C3 alkyl, amino or hydroxyl.

In another preferred embodiment, Ar is benzene or substituted benzene with substituent selected from halogen, C1-C3 alkyl, amino or hydroxyl.

On the second aspect of this invention, the invention provides a method for preparing the compound represented by Formula 1 or pharmaceutically acceptable salt thereof, comprising the steps of:

(a) reacting polyene antibiotic or its salt with a halogen-containing ester compound in an organic solvent, to produce the polyene diester compound represented by formula 1:

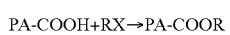

Wherein, PA is selected from the following polyene antibiotic nuclear parent:

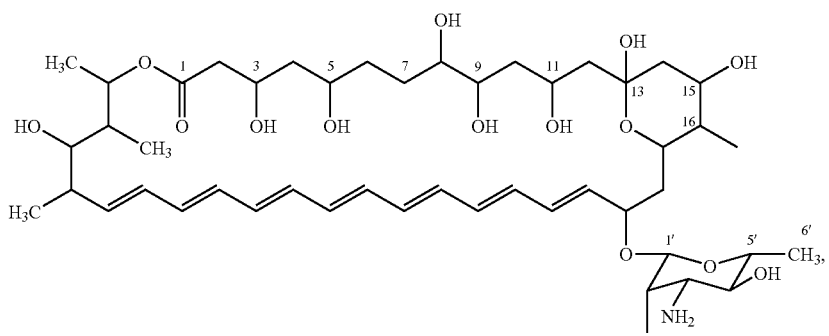
2
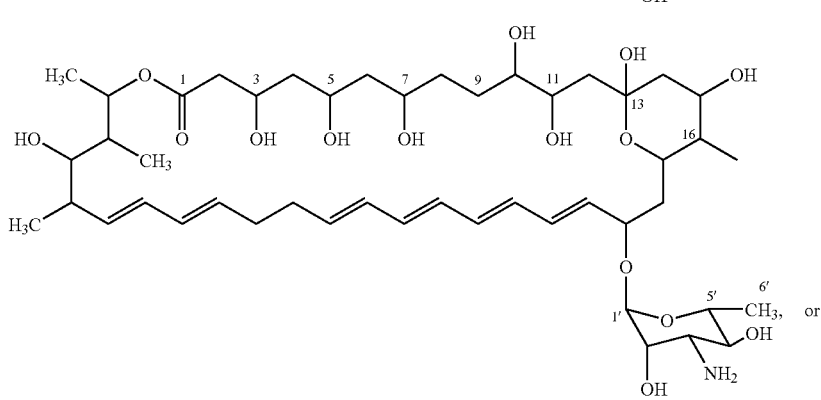
3 or
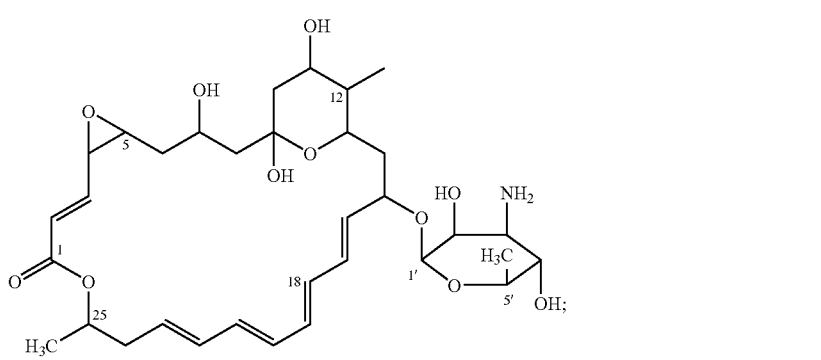
4
R is linear or cyclic carbonate or carboxylic acid ester group;
X=Cl, Br, or I;
(b) separating to give polyene diester compound represented by formula 1.
In another preferred embodiment, said PA has the following stereostructure:
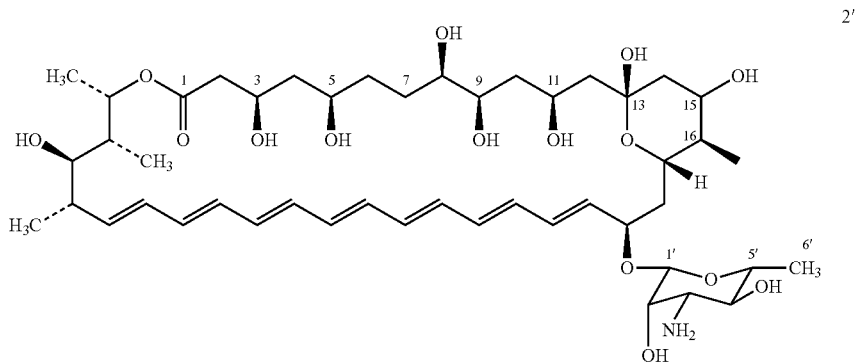
2'

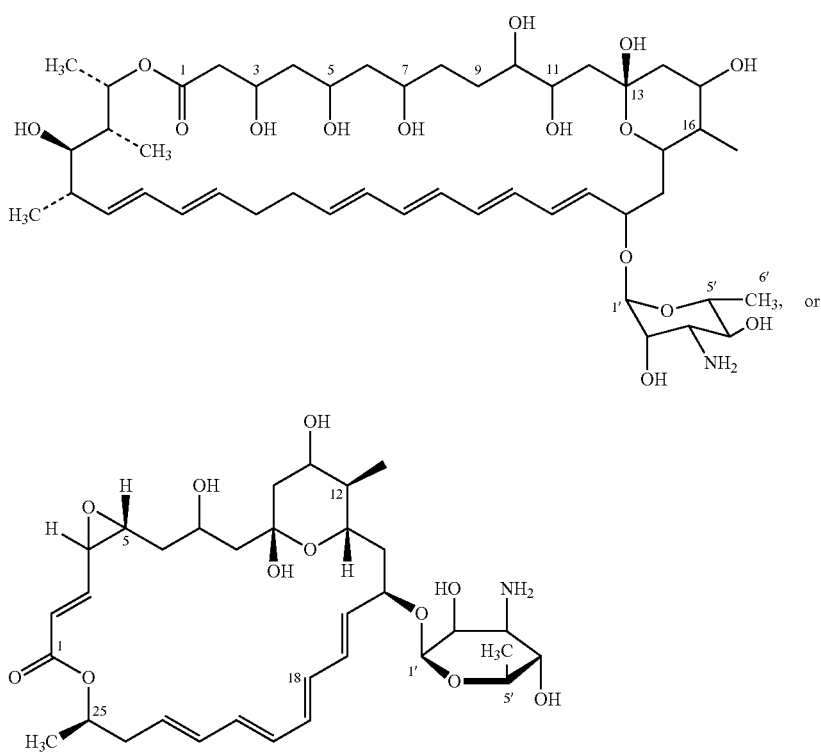

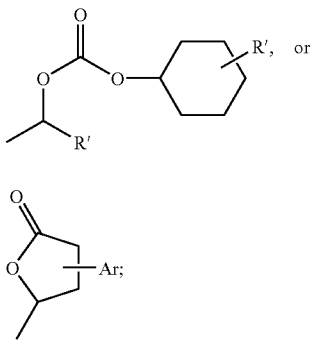

In another preferred embodiment, said organic solvent is selected from: dimethylformamide, dimethyl sulfoxide, tetrahydrofuran, acetonitrile, etc.

In another preferred embodiment, R is selected from:

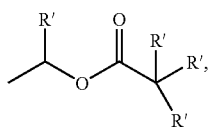

18

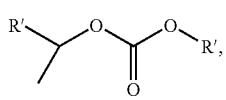

19

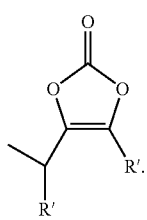

20

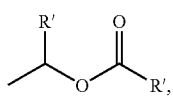

21

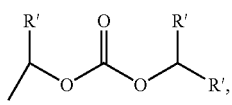

22

23

11 wherein, R' is selected from halogen, C1-C3 alkyl or hydroxyl;

Ar is selected from aryl, hetero aromatic rings containing nitrogen, sulphur, oxygen, or substituted aryl or hetero aromatic rings containing nitrogen, sulphur, oxygen, with 1-3 substituents selected from halogen, C1-C3 alkyl, amino or hydroxyl.

In another preferred embodiment, R is selected from:

5

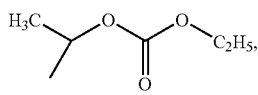

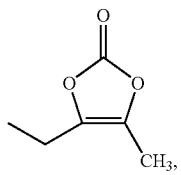

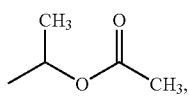

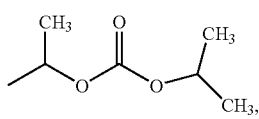

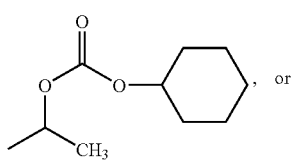, or

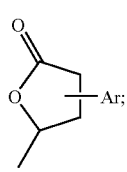

Wherein, Ar is selected from aryl, hetero aromatic rings containing nitrogen, sulphur, oxygen, or substituted aryl or hetero aromatic rings containing nitrogen, sulphur, oxygen, with 1-3 substituents selected from halogen, C1-C3 alkyl, amino or hydroxyl.

In another preferred embodiment, in step (a), polyene antibiotic or its salt and halogen-containing ester compound react in an aprotic solvent.

In another preferred embodiment, said aprotic solvent is selected from: dimethylformamide, or dimethyl sulfoxide.

In another preferred embodiment, said salt of the compound represented by Formula 1 is organic alkali salt or inorganic alkali salt, such as triethylamine salt, sodium salt.

In another preferred embodiment, said halogen-containing ester compound is selected from the group consisting of: iodomethyl pivalate, 1-iodoethyl isopropyl carbonate, chloromethyl pivalate, 1-bromoethyl acetate, 1-iodoethyl ethyl carbonate, 1-iodoethyl cyclohexyl carbonate, 4-bromomethyl-5-methyl-1,3-dioxol-2-one, or 3-iodo-1 (3H)-isobenzofuranone, etc.

In another preferred embodiment, an organic or inorganic alkali is added in step (a).

In another preferred embodiment, step (a) also include step (a'): adding NaI.

In another preferred embodiment, said organic alkali in step (a) is selected from but not limited to: triethylamine, N,N-dimethylaniline, pyridine, quinoline, 1,8-Diazabicyclo [5,4,0]-undec-7-ene (DBU), 1,5-diazabicyclo[4.3.0]non-5-ene (DBN) or tetramethyl guanidine, etc.

In another preferred embodiment, said inorganic alkali in step (a) is selected from but not limited to: NaOH (KOH), $Na_2CO_3$ ($K_2CO_3$), $NaHCO_3$ ($KHCO_3$), $Na_2HPO_4$ ($K_2HPO_4$), etc.

In another preferred embodiment, step (a) is carried out at pH of 7.2-11, preferably 7.5-9.5.

In another preferred embodiment, nitrogen is introduced into the reaction of step (a).

In another preferred embodiment, an organic solvent is added into the raw product produced by the reaction, the resulting mixture is filtered to remove unreacted raw material and insoluble impurity, and the solution is treated with decolouring treatment, concentrated and dried to give the product. Said organic solvent is alcohol, ketone, halohydrocarbon, ester, aromatic, etc. and preferably the organic solvent is methanol, ethanol, acetonitrile, tetrahydrofuran, or acetone, ethyl acetate, methyl acetate. In another preferred embodiment, drying step, such as vacuum drying, is included.

On the third aspect of this invention, the invention provides a pharmaceutical composition, which contains therapeutically effective amount of the compound represented by formula 1 or pharmaceutically acceptable salt thereof and a pharmaceutically acceptable carrier.

In another preferred embodiment, said pharmaceutical composition is selected from the following formulations: granule formulation, powder formulation, tablet, capsule, syrup, suppository, injection, emulsion, tincturae, suspension, solution, administrated in the form of oral administration or parenteral administration. Alternatively, it may be used externally.

On the fourth aspect of this invention, the invention provides a method for preparing the pharmaceutical composition, including the steps of: mixing the compound represented by formula 1 or the pharmaceutically acceptable salt thereof with the pharmaceutically acceptable carrier, therefore to form the pharmaceutical compound.

On the fifth aspect of this invention, the invention provide use of the compound represented by formula 1 or the pharmaceutically acceptable salt thereof in the preparation of antifungal or anti-HIV drug.

On the sixth aspect of this invention, the invention provides a method for anti fungal or treating HIV, including the steps of: administrating therapeutically effective amount of the compound represented by formula 1 or pharmaceutically acceptable salt thereof to the patient.

Based on these, this invention provides a new polyene antibiotics ester derivative, which can be hydrolyzed by the esterase in vivo, with mild conditions, not easy to be destroyed, and has good effect and low toxicity.

DETAILED DESCRIPTION

Figure 1:
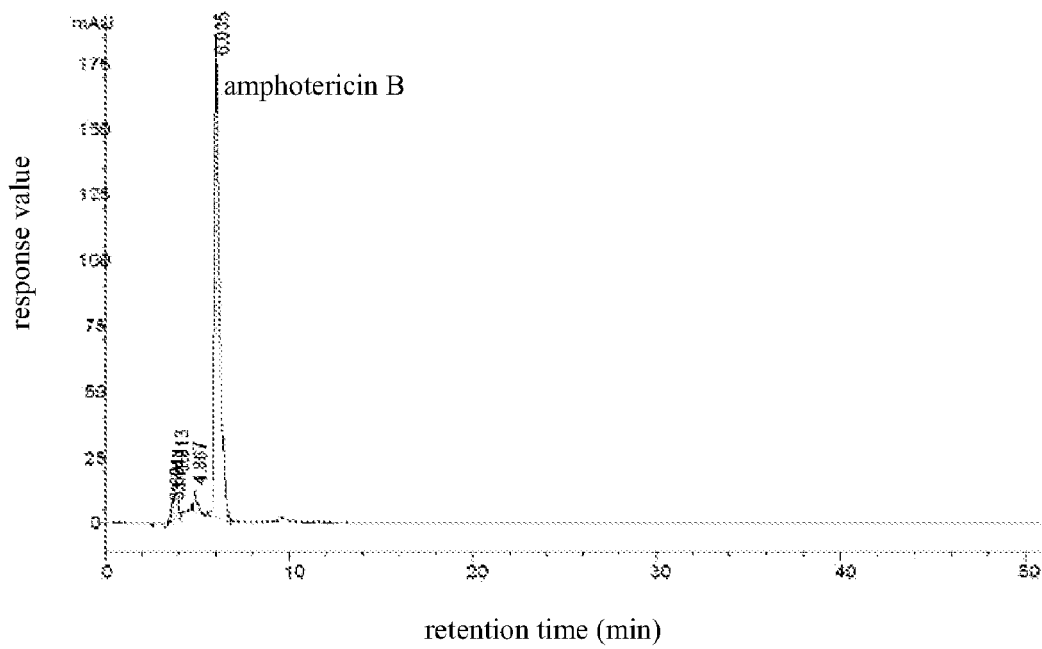
FIG. 1 shows the chromatogram of amphotericin B under the HPLC test conditions according to this invention.

After extensive and intensive research, the present inventors use the diester prodrug of amphotericin B, mycostatin, natamycin to improve their absorption; and they are hydrolyzed into original drug by the esterase in vivo to show pharmacodynamic effect. Therefore, their absorption in vivo can be increased greatly, their plasma concentration is increased and their half-life is prolonged, so that their therapeutic effects are improved or their dosage is reduced.

Particularly, by using the carboxylic group of amphotericin B, mycostatin, or natamycin to produce diester, their absorption and therapeutic effects can be improved so as to achieve the purpose of lowering their dosage and toxicity.

Besides, as the diester can be hydrolyzed by esterase in vivo, it is not necessary to hydrolyze by chemical method such as acid and/or alkali, therefore the reaction condition is mild and the product will not be destroyed by acid and/or alkali.

As used herein, PA refers to polyene antibiotic nuclear parent which does not contain ester group, particularly, it is selected from the compounds of formula 2, 3 or 4, preferably from the stereostructure of the compounds of 2, 3 or 4, namely formula 2', 3' or 4'.

As used herein, amphotericin B refers to the compound with the structure as shown in formula 15.

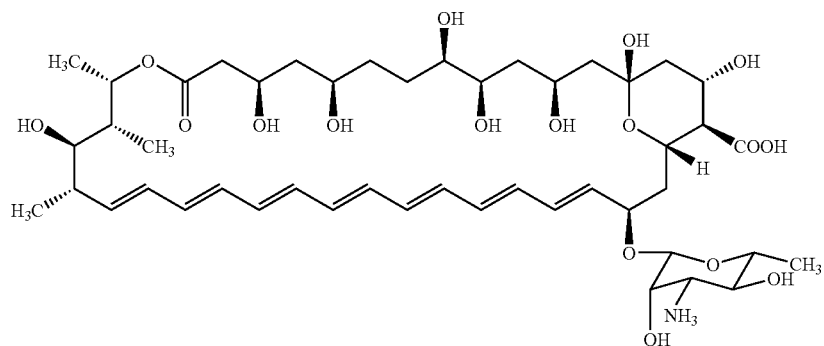

15

As used herein, mycostatin refers to the compound with the structure as show in formula 16.

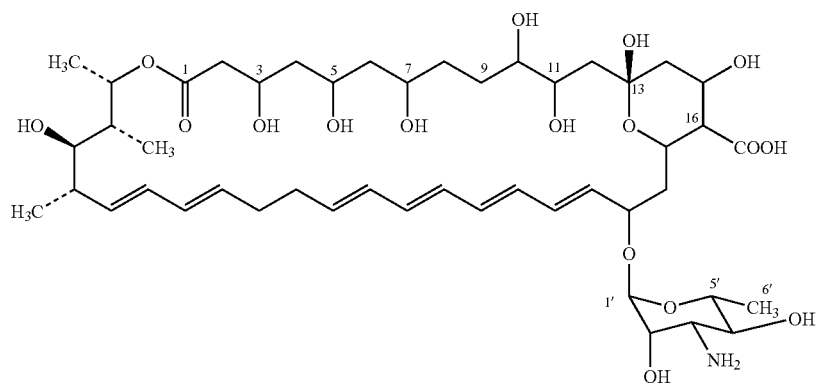

16

As used herein, natamycin refers to the compound with the structure as show in formula 17.
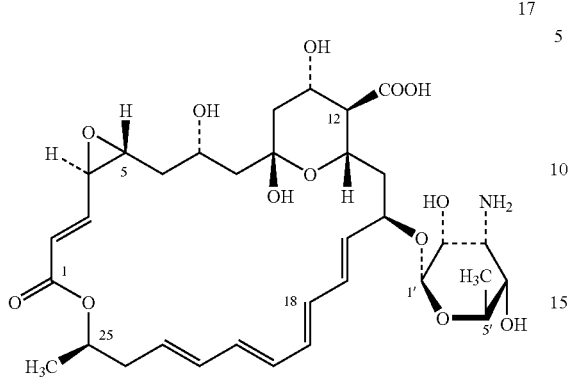
17
The Compound
This invention provides a polyene antibiotic diester derivative, whose structure is shown in formula 1, particularly, it is selected from compounds of formulas 12, 13, or 14.
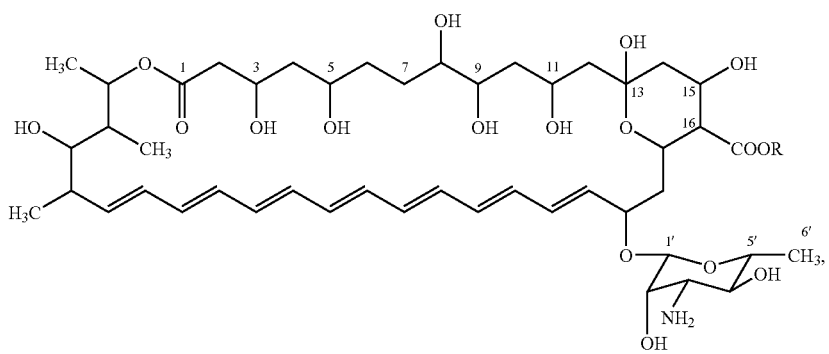
12
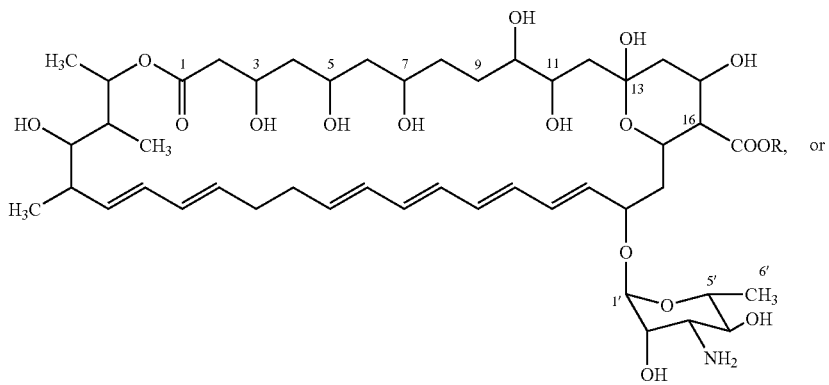
13
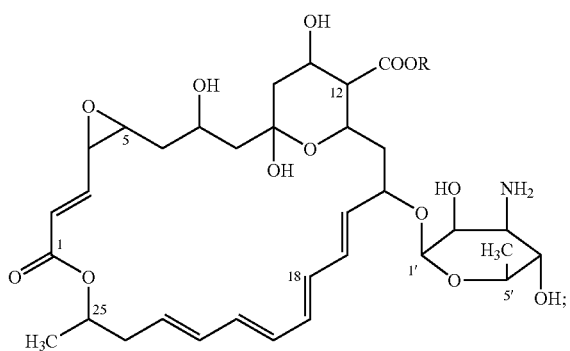
14

Preferably, compound of formula 1 has the stereostructure of formulas 12', 13' or 14':

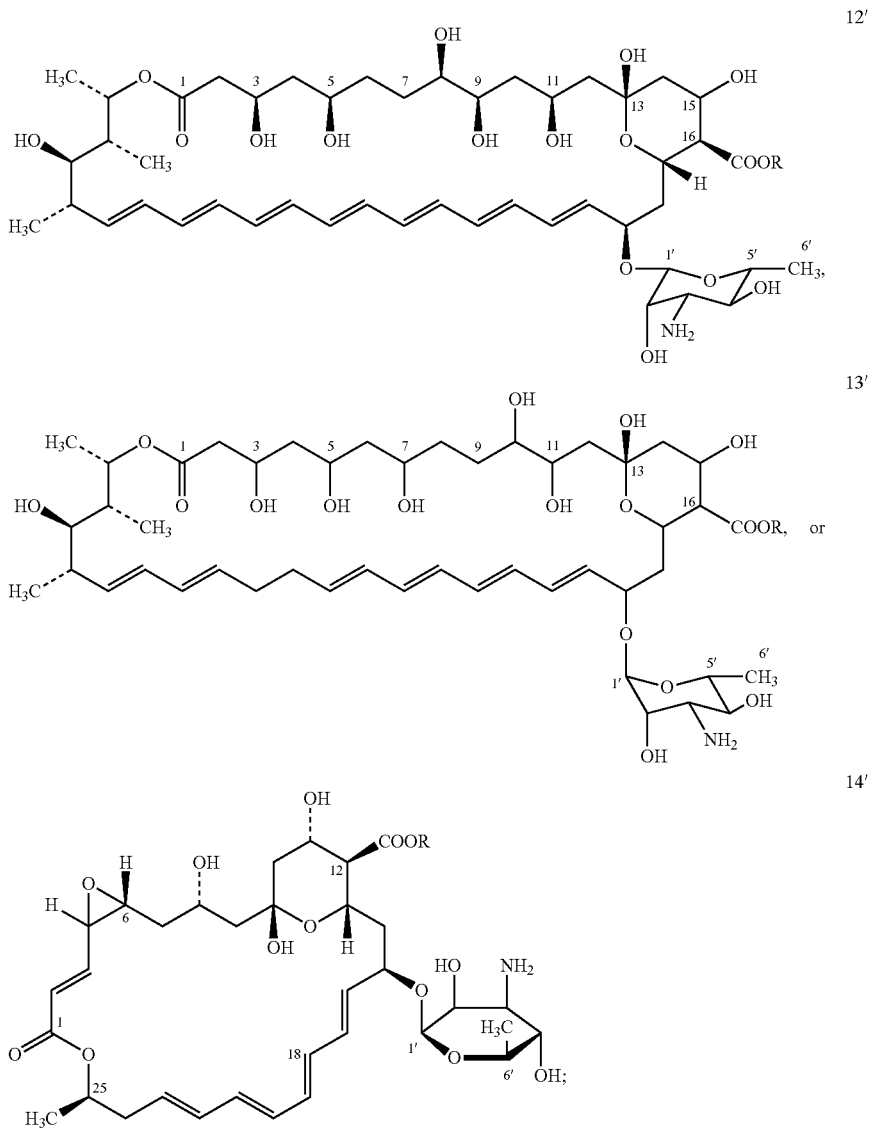

Wherein, R is linear or cyclic carbonate or carboxylic acid ester group. Preferably, R is a group containing 2-15 carbon atoms and having 1-3 liner or cyclic carbonate or carboxylic acid ester groups. More preferably, R contains 2-10 carbon atoms. Still more preferably, R is selected from the group consisting of the following structure formulas:

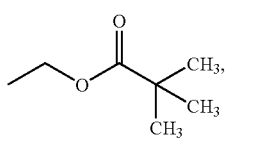

5

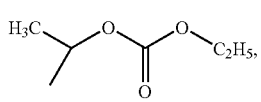

6

-continued

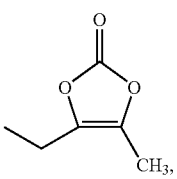

7

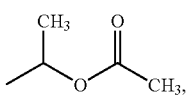

8

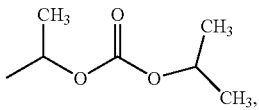

9

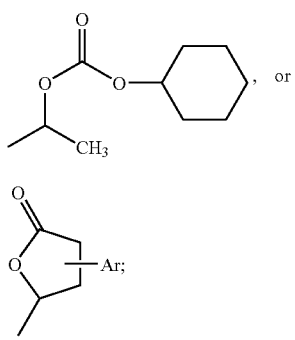

Wherein, Ar is selected from aryl, hetero aromatic rings containing oxygen, sulphur, nitrogen, or substituted aryl, or substituted hetero aromatic rings containing oxygen, sulphur, nitrogen; preferably, the substituent of the substituted aryl or substituted hetero aromatic rings is selected from halogen, C1-C3 alkyl, amino or hydroxyl; more preferably, Ar is phenyl.

The polyene diester compound provided by this invention can form pharmaceutically acceptable acid addition salt with inorganic acid or organic acid, wherein said inorganic acid can be hydrochloric acid, sulfuric acid, and phosphoric acid, and the organic acid can be oxalic acid, fumaric acid, maleic acid, malic acid, citric acid, tartaric acid, glutamic acid, lactic acid, lactobionic acid, deoxycholic acid, etc.

The Preparation of the Compound

According to this invention, the compound represented by formula 1 can be prepared by the methods known in the art, in some preferred embodiments, the starting raw materials is amphotericin B, mycostatin, or natamycin as shown in formulas 15, 16 or 17. The amphotericin B, mycostatin, or natamycin can be purchased commercially, or be produced by the methods known in the art.

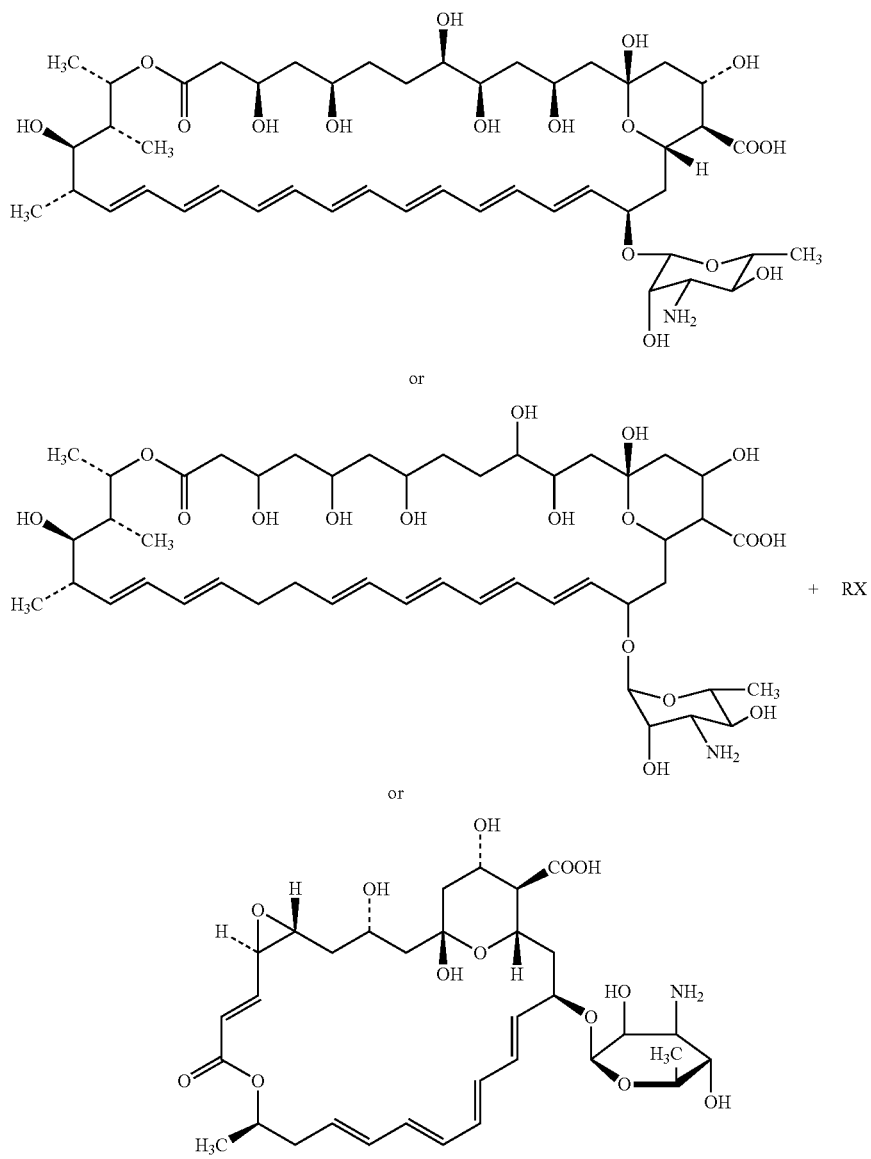

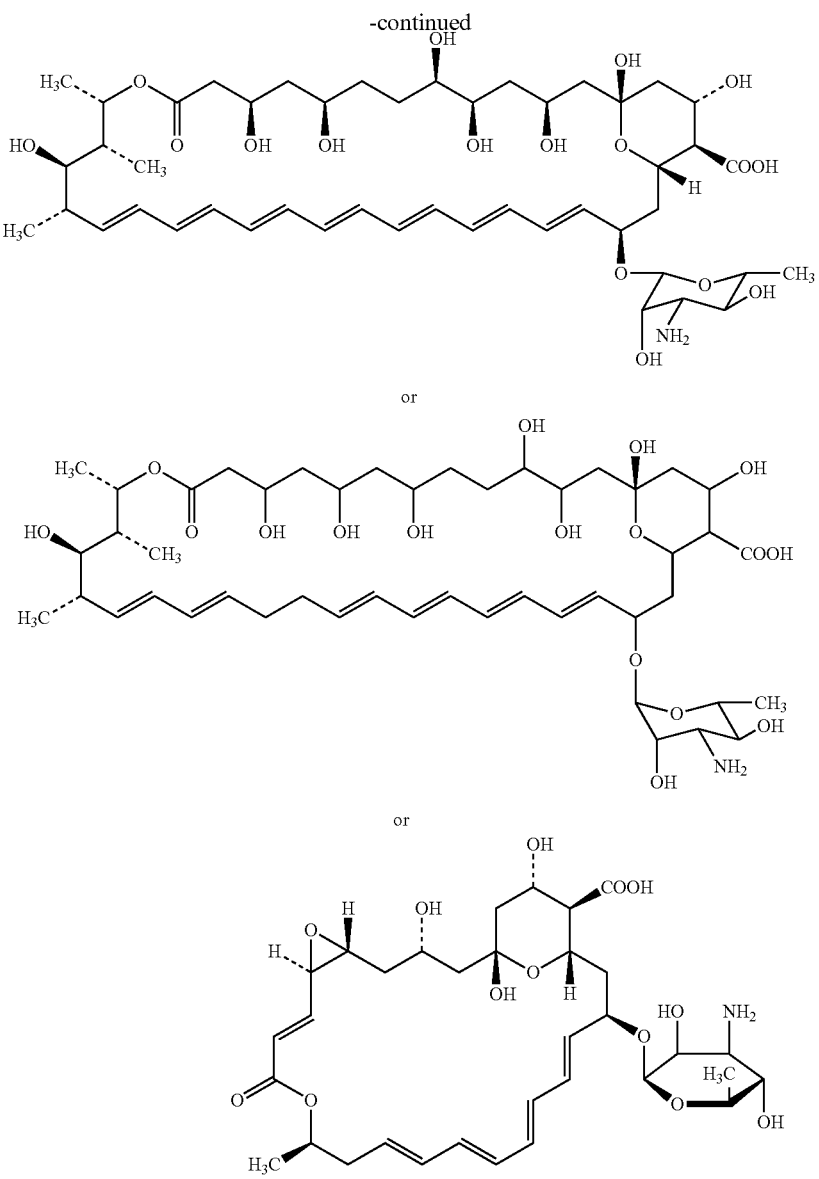

In the formula, R is a group containing 2-15 carbon atoms and having 1-3 liner or cyclic carbonate or carboxylic acid ester groups; X=Cl, Br, or I.

When the reactants are compounds as shown in formulas 15, 16 or 17, NaI can be introduced into the reaction system to make the reaction easier to carry out.

The reactants also can be salts of the compounds as shown in formulas 15, 16, or 17, and said salts is selected from: sodium salt, potassium salt, calcium salt, magnesium salt, triethylamine salt, preferably selected from organic alkaline salt, sodium salt.

According to this invention, polyene antibiotics and halogen-containing ester compounds react under alkaline condition, to produce reaction mixture containing polyene diester compound, and then said reaction mixture is separated to give polyene diester compound.

One preferred method is to resolve amphotericin B, mycostatin, or natamycin in dimethylformamide (or dimethyl sulfoxide), charge nitrogen, add alkaline agent under ≦0° C., and then add halogen-containing ester compound to carry out reaction. After the reaction is finished, the product is decoloured and filtered, and the filtrate is concentrated and dried to give final product.

Said halogen-containing ester compound contains 2-15 carbon atoms, and 1-3 halogen atoms, preferably 2-10 carbon atoms, and 1 halogen atom. Some preferred embodiments contain structures of 5-11, including but not limited to: iodomethyl pivalate, chloromethyl pivalate, 1-iodoethyl isopropyl carbonate, 1-bromoethyl acetate, 1-iodoethyl cyclohexyl carbonate, 1-iodoethyl ethyl carbonate, 4-bromomethyl-5-methyl-1,3-iodo-1, or 3-dioxol-2-one (3H)-isobenzofuranone.

An alkaline substance may be added in the reaction to make pH 7.2-11, and said alkaline substance include organic alkaline and inorganic alkaline, preferably selected from triethylamine, N,Ndimethylaniline, pyridine, quinoline, 1,8-Diazabicyclo[5,4,0]-undec-7-ene (DBU). The pH of the reaction system is 7.2-11, preferably 7.5-9.5. Preferably, the reaction temperature is 0~−30° C., more preferably −5~−20° C. Preferably the reaction time is 20 mins to 5 hours, more preferably 0.5-3.5 hours.

In the reaction, the methods well known can be used to decolour the product, one preferred method is to use active carbon.

The methods known in the art can be used to wash and filter the reaction product, and one preferred method is to use organic solvent, such as alcohol, ether, ester or ketone, more preferably, to use methanol, ethanol, ethyl acetate or acetone, ethyl ether, isopropyl ether.

After filtering the insoluble, the method known in the art is used to concentrate the filtrate until solid is precipitated, and then the precipitated solid is collected and dried by using the method known in the art to give final product, and one preferred method is to vacuum dry under 30-50° C.

The Pharmaceutical Composition

Therapeutically effective amount of the polyene diester compound represented by formula 1 and pharmaceutically acceptable carrier, are mixed to produce a form of composition; wherein based on the weight of the composition, the therapeutically effective amount of the compound represented by formula 1 is 0.1-99% (w/w).

According to this invention, the composition could exist in forms of many formulations. Said formulations can be granule formulation, powder formulation, tablet, capsule, syrup, suppository, injection, emulsion, tincture, suspension, solution, administrated in the form of oral administration or non-oral administration.

For oral administration, tablet, pastille, capsule, pill, powder, granule, paste, suspension, emulsion or solution can be used.

For non-gastrointestinal administration, injection, infusion solution, suppository, patch, etc. can be used.

For intraarticular injection, suspension prepared by corresponding method can be used.

For intramuscular injection, water solution and oil solution and corresponding depot formulation can be used.

For external and topical administration, lotion, cream, gel, ointment, film, etc. can be used.

The effective amount of the active component being used can vary according to the model of administration and the seriousness of the disease to be treated. However, generally, according to this invention, when the compound is administrated at a dose of about 0.5-200 mg/kg animal weight every day, desirable effect can be achieved, and more preferably, the amount of the compound is divided by administrating 2-4 times every day, or administrated in the form of sustained release. For most of the large mammal animals, the total dose is 1-500 mg per day.

According to this invention, when the polyene diester compound prepared according to the above mentioned method is used as vascular targeting agent, this medicament can be administrated by oral administration or parenteral administration, such as muscle, subcutaneous, intravenous routine and suppository and other forms. The dose of the medicament can vary according to the development degree of the disease, normally between 1 and 3000 mg for adult.

For intravenous administration, the maximum dose per day is not more than 3-100 mg/kg for adult, accumulative dose and the course of treatment depend on the variety of disease, and the concentration of the infusion liquid is 3-20 mg/100 ml. The concentration of intrathecal injection drug is 10-50 mg/100 ml, which may be slowly injected, and the maximum amount of the intrathecal injection is no more than 1-3 mg at one time, the total amount is 5-30 mg. Local administration: for aerosol inhalation 2-30 mg for adult every time; for ultrasonic spray inhalation the concentration of the product is 0.01-0.1%, 2-3 times per day, 2-25 ml every time; for continuous bladder irrigation, adding 2-10 mg into 100 ml of sterile injectable water and washing at a rate of 40 ml per hour every day, 3-15 days in total.

In preferred embodiment, the compound according to this invention can be administrated through oral administration, and intravenous, intramuscular or subcutaneous administration. Solid carrier includes: starch, lactose, calcium hydrogen phosphate, microcrystalline cellulose, sucrose and kaolin; and liquid carrier includes: sterile water, polyethylene glycol, nonionic surfactant and edible oil such as corn oil, peanut oil and sesame oil, as long as they are suitable for the property of the active component and the specific way of administration. In the preparation of the pharmaceutical composition, the commonly used adjuvant can also be favorably included, such as flavoring agent, pigment, preservative, antioxidant (for example, Vitamin E, Vitamin C, butylated hydroxytoluene (BHT) and butylated hydroxyanisole(BHA)).

As used herein, the term of "non-oral" includes: subcutaneous injection, patch (skin absorption), intravenous injection, intraperitoneal injection and drip infusion, using suitable dispersant or lubricant and suspension agent, and injection formulation such as aqueous or oily suspension for sterile injection could be prepared by the normal methods in the art. The formulation for sterile injection could be nontoxic non-oral administrated solution or suspension in diluent or solution, such as water solution, the usable carrier or solvent include water and isotonic saline, and nontoxic non-volatile oil can also be used as solvent or suspending medium. Therefore, any non-volatile oil or fatty acid could be used, including natural, synthetic or semi synthetic fatty oil and fatty acid, and natural, synthetic or semi synthetic mono-glyceride, diglyceride or triglyceride.

The suppository for rectal administration could be prepared by mixing the drug with a suitable inirritative excipient, wherein the excipient is solid under normal temperature, and is liquid under the enteral temperature in order to dissolve and release the drug into recta, such as cocoa butter or polyethylene glycol.

According to this invention, the pharmaceutical composition containing polyene diester compound could be prepared by mixing therapeutically effective amount of the polyene diester compound with pharmaceutically acceptable carrier.

According to this invention, the polyene diester could be formulated into oral formulation, including tablet, capsule. These formulations could be prepared by mixing the active component with at least one additive, wherein the additive includes excipient, binder, disintegrating agent, lubricant, colorant, flavoring agent, etc. and the formed mixture could be made into formulations such as powder formulation, granule formulation, tablet, coated tablet, pill, capsule, etc. The excipient includes one or more of lactose, corn starch, carbohydrate, glucose, sorbitol, crystalline cellulose. The binder includes one or more of polyvinyl alcohol, methylcellulose, ethyl cellulose, arabic gum, tragacanth, gelatin, lac, cellulose hydroxypropyl, hydroxypropyl starch, polyvinylpyrrolidone. The disintegrating agent includes one or more of starch, agar, gel powder, crystalline cellulose, calcium carbonate, sodium bicarbonate, calcium citrate, cyclodextrin, pectin. The lubricant includes one or more of magnesium stearate, talc, polyethylene glycol, silica, hydrogenated vegetable oil. The colorant includes pigments allowed to be added into drugs. The flavoring agent includes cocoa powder, menthol, peppermint oil, refined borneol, and cinnamon. If necessary, those tablet and granule formulation could be coated with cane sugar, gelatin, etc. These formulation can also include other additives, including inert diluent, preservative such as p-hydroxybenzoate, sorbic acid, antioxidant such as vitamin C, a-vitamin E and cysteine, decomposer, binder, thickener, buffer, sweetener, condiment, and perfume. The tablet and pill can also be coated with enteric material. Oral administrated liquid formulation includes pharmaceutically usable emulsion, syrup, tincture, suspension and solution, and can include normal inert diluent, such as water.

From the point of easy preparation and administration, the preferred pharmaceutical composition is solid composition, especially tablet and solid filled or liquid filled capsule. Oral administration of the composition is preferred.

When using the compound according to this invention for anti-fungal treatment, other anti-bacterial or antiviral methods or other therapeutic agent can be used in combination. For example, one or more auxiliary active component from the following group can be combined: azole or non-azole anti-fungal drug.

The advantages of the invention include:
1. The antimicrobial effects of the polyene diester compound according to this invention are good and the safety is also improved at the same time;
2. The polyene diester compound according to this invention can be hydrolyzed by esterase in vivo, with no necessity of chemical methods such acid and/or alkaline, therefore the product is not easy to be destroyed.

This invention will be further described with the following specific examples. It should be understood that these examples are solely for the explanation of this invention but not to limit the scope of the invention. The specific conditions of the experiment method which are not specified in the examples are generally the normal conditions or according to the suggested conditions by the manufacturer. Unless otherwise specified, all the percentage and parts are by weight

EXAMPLE 1

The preparation of amphotericin B methyl pivalate

Dissolving 230.8 mg (0.25 mmol) of amphotericin B in 2 ml of DMF, cooling to −10° C. and adding 0.07 ml of pyridine under nitrogen stream, stirring for 5 minutes, adding 181.5 mg (0.75 mmol) of iodomethyl pivalate and reacting for 1 hour, adding 25 ml ice water, after the treatment, collecting and filtering the precipitated deep yellow solid, compressing to dry and then adding 15 ml of ethanol, removing the insoluble substance, concentrating the filtrate until almost dry, collecting the precipitated yellow solid, drying in vacuum at 40° C. to give 24.8 mg of amphotericin B methyl pivalate, with a yield of 9.6%.
MS ES+: M+H 1038.25

EXAMPLE 2

The preparation of amphotericin B isopropoxycarbonyloxyethyl ester

Dissolving 461 mg (0.5 mmol) of amphotericin B in 3 ml of DMF, cooling to 0° C. and adding 153 mg of 40 DBU, stirring for 5 minutes, then immediately adding 219 mg (0.85 mmol) of 1-iodoethyl isopropyl carbonate, and strongly stirring for 3 hours, using thin layer chromatography to trace the reaction, after the reaction almost finishes, adding 70 ml ice water, stirring for 10 minutes and then standing for 2 hours, filtering and collecting, washing by 3 ml×3 of water, dissolving the deep yellow solid in methanol, adding activated carbon to decolor, concentrating the filtrate under reduced pressure until solid is precipitated, cooling and standing overnight, filtering, using a little diluted methanol to wash twice, drying at 40° C. to give 43.6 mg of yellow solid amphotericin B isopropoxycarbonyloxyethyl ester, with a yield of 8.3%.
MS ES+: M+H 1054.15

EXAMPLE 3

The preparation of amphotericin B ethoxycarbonyloxyethyl ester

Dissolving 230.8 mg (0.25 mmol) of amphotericin B in 2 ml of DMF, reacting with 244 mg (1 mmol) of 1-iodoethyl ethyl carbonate, preparing 26.3 mg of amphotericin B ethoxycarbonyloxyethyl ester according to the method as described in example 2, with a yield of 10.1%. MS ES+: M+H 1040.02

EXAMPLE 4

The preparation of amphotericin B cyclohexyloxycarbonyloxyethyl ester

According to the method as described in example 2, reacting 230.8 mg (0.25 mmol) of amphotericin B with 298 mg (1 mmol) of 1-iodoethyl cyclohexyl carbonate, to prepare 28.8 mg of amphotericin B cyclohexyloxycarbonyloxyethyl ester, with a yield of 10.5%. MS ES+: M+H 1094.59

EXAMPLE 5

The preparation of amphotericin B ethyl acetate

According to the method as described in example 2, reacting 230.8 mg (0.25 mmol) of amphotericin B with 83.5 mg (0.5 mmol) of 1-bromoethyl acetate, to prepare 17.8 mg of amphotericin B ethyl acetate, with a yield of 7.1%.
MS ES+: M+H 1010.37

EXAMPLE 6 amphotericin B-5-methyl-1,3-dioxol-2-one-4-methyl ester

Reacting 230.5 mg (0.25 mmol) of amphotericin B with 386 mg (2 mmol) of 4-bromomethyl-5-methyl-1,3-dioxol-2-one, according to the method as described in example 10, to prepare 20.6 mg of amphotericin B-5-methyl-1,3-dioxol-2-one-4-methyl ester, with a yield of 7.96%. MS ES+: M+H 1036.21

EXAMPLE 7 amphotericin B-1, 3-2H-3-oxo-1-isobenzofuran ester

According to the method as described in example 2, reacting 230.8 mg (0.25 mmol) of amphotericin B with 520 mg (2 mmol) of 3-iodo-phthalide, to prepare 25.3 mg of target product, with a yield of 9.7%. MS ES+: M+H 1040.48

EXAMPLE 8

The preparation of mycostatin methyl pivalate

Dissolving 474 mg (0.5 mmol) of mycostatin sodium in 5 ml of DMF, cooling to −15° C. and adding 242 mg (1 mmol) of iodomethyl pivalate under nitrogen stream, and strongly stirring for half an hour, adding 150 ml of water after the reaction is completed, after the treatment, filtering the precipitated solid, washing by water, to obtain the dry raw product of 580 mg. Dissolving 550 mg of the raw product in 20 ml of ethanol, adding activated carbon to decolor and filtering the insoluble substance, concentrating the filtrate under reduced pressure, filtering and collecting, precipitating yellow solid, washing by a little diluted ethanol and drying, to give 55.8 mg of light yellow solid mycostatin methyl pivalate, with a yield of 10.7%.

MS ES+: M+H 1040.07

EXAMPLE 9

The preparation of mycostatin methyl pivalate

Dissolving 463 mg (0.5 mmol) of mycostatin in 3 ml of DMF, cooling to −5° C. and adding 0.2 ml of triethylamine, pH=8-9, adding 370 mg of NaI and 110 mg(0.73 mmol) of chloromethyl pivalate under nitrogen stream, and strongly stirring for one hour, adding 60 ml of water, after the treatment, collecting and filtering the solid and washing by water for multiple times, compressing to dry, adding 30 ml of ethyl acetate, filtering the insoluble substance, concentrating the filtrate under reduced pressure to almost dry, to give 29.3 mg of light yellow solid mycostatin methyl pivalate, with a yield of 5.6%.

MS ES+: M+H 1040.20

EXAMPLE 10

The preparation of mycostatin ethyl acetate

Dissolving 231 mg (0.25 mmol) of mycostatin in 1 ml of DMSO, cooling to −20° C., adding 80 mg of DBU, adding 83.5 mg of bromoethyl acetate while stirring, reacting for 3 hours and then adding 25 ml water, precipitating solid, collecting and filtering, washing by water, compressing to dry, adding 15 ml acetone, filtering the solution to remove the insoluble substance, combining the acetone filtrate, concentrating under reduced pressure to almost dry, filtering and collecting the solid and drying at 40° C., to give 18.8 mg mycostatin ethyl acetate, with a yield of 7.4%.

MS ES+: M+H 1012.20

EXAMPLE 11

Natamycin methyl pivalate

Taking 332.5 mg (0.5 mmol) natamycin and dissolving in 2 ml DMF, cooling to −5° C., adding 0.14 ml (1.0 mmol) triethylamine under nitrogen stream, after stirring for 5 minutes, adding 484 mg (2 mmol) 35 iodomethyl pivalate, strongly stirring for 1 hour, adding into isopropyl ether, precipitating solid, washing by water after filtering, collecting and filtering solid, vacuum drying, adding isopropanol, filtering the insoluble substance, concentrating the filtrate until almost dry, precipitating solid, vacuum drying, to give natamycin methyl pivalate 50.1 mg, with a yield of 12.8%. MS ES+: M+H 780.03

EXAMPLE 12

The preparation of natamycin ethoxycarbonyloxyethyl ester

According to the method as described in example 2, reacting 332.5 mg (0.5 mmol) natamycin with 244 mg (1 mmol) 1-iodoethyl ethyl carbonate, precipitating raw product, filtering the insoluble substance, concentrating the filtrate, precipitating solid, collecting and filtering, drying to give 31.8 mg natamycin ethoxycarbonyloxyethyl ester product, with a yield of 8.1%. MS ES+: M+H 782.12

TABLE 1

| | structural formula | R |
|---|---|---|
| Example 1 | (structure shown) | (ethyl isobutyrate group) 5 |
| Example 2 | (structure shown) | (diisopropyl carbonate group) 9 |

TABLE 1-continued

| | structural formula | R |
|---|---|---|
| Example 3 | Amphotericin B derivative structure with numbered positions 1,3,5,7,9,11,13,15,16 and 1',5',6',12' on sugar moiety; macrolide with polyene chain, COOR group, and mycosamine sugar bearing NH₂ and OH groups | $H_3C$—CH(CH₃)—O—C(=O)—O—$C_2H_5$  6 |
| Example 4 | Amphotericin B derivative structure with numbered positions 1,3,5,7,9,11,13,15,16 and 1',5',6',12' | isopropyl cyclohexyl carbonate structure  10 |
| Example 5 | Amphotericin B derivative structure with numbered positions 1,3,5,7,9,11,13,15,16 and 1',5',6',12' | $CH_3$—CH(CH₃)—O—C(=O)—$CH_3$  8 |
| Example 6 | Amphotericin B derivative structure with numbered positions 1,3,5,7,9,11,13,15,16 and 1',5',6',12' | 4-ethyl-5-methyl-1,3-dioxol-2-one  7 |

TABLE 1-continued
| | structural formula | R |
|---|---|---|
| Example 7 | 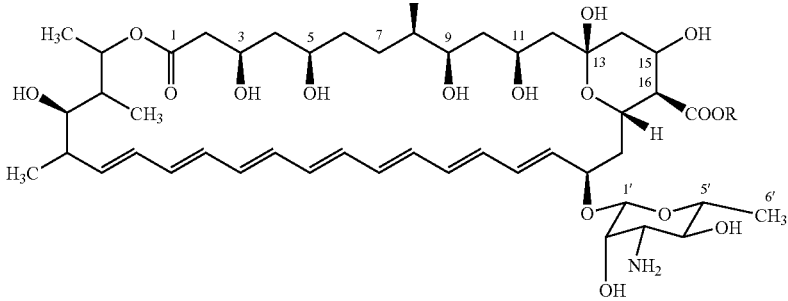 12' | 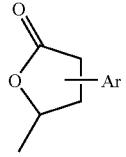 11 wherein Ar is benzene: 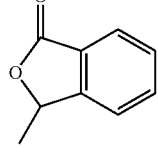 |
| Example 8 | 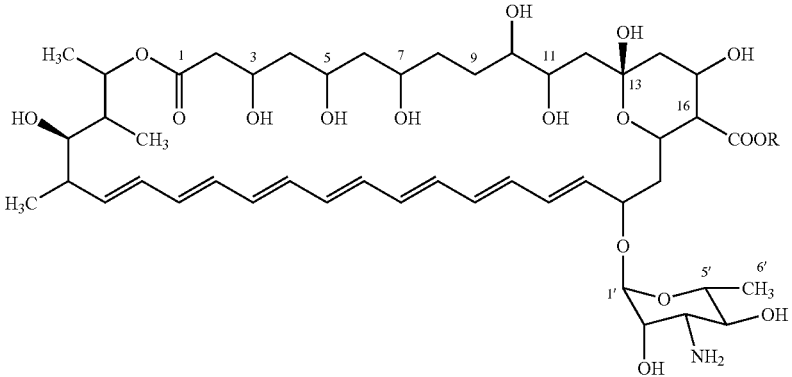 13' | 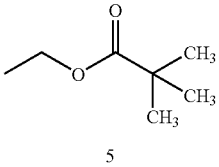 5 |
| Example 9 | 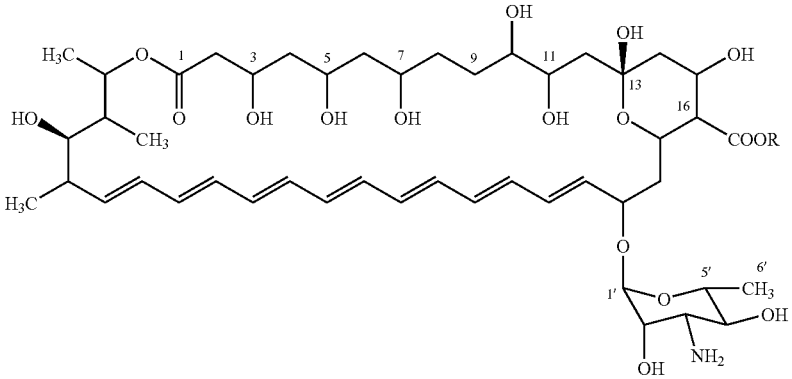 13' | 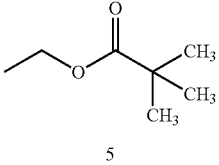 5 |
| Example 10 | 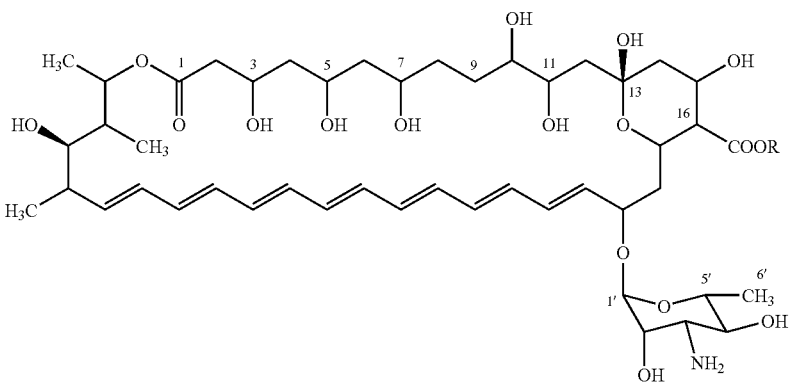 13' | 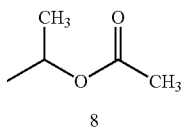 8 |

TABLE 1-continued

| | structural formula | R |
|---|---|---|
| Example 11 | [structure showing macrolide with OH, COOR at position 12, epoxide, sugar moiety with NH₂, OH, H₃C groups, positions 1, 5, 12, 18, 25, 1', 5', 14'] | [ethyl 2,2-dimethyl-propanoate ester group: CH₃CH₂–O–C(=O)–C(CH₃)₂–] 5 |
| Example 12 | [structure showing macrolide with OH, COOR at position 12, epoxide, sugar moiety with NH₂, OH, H₃C groups, positions 1, 5, 12, 18, 25, 1', 5', 14'] | [isopropyl ethyl carbonate group: (CH₃)₂CH–O–C(=O)–O–C₂H₅] 6 |

EXAMPLES 13-24

Test of Antibacterial Activity In Vitro

Materials and Methods:

1. Drugs

Experiment drugs: the polyene diester compounds prepared by examples 1-12

Control drugs: amphotericin B (standard product)
mycostatin (standard product)
natamycin (standard product)

2. Strains 2.1 Preparation of *Candida albicans* suspension: PHARMACOPOEIA OF THE PEOPLES REPUBLIC OF CHINA, second part, 2005 edition, appendix p 81-84.

2.2 Preparation of *Saccharomyces cerevisiae* suspension: PHARMACOPOEIA OF THE PEOPLES REPUBLIC OF CHINA, second part, 2005 edition, appendix p 80, p 83.

2.3 Preparation of *Candida* mycoderrna suspension: the method is as same as preparation of *Saccharomyces cerevisiae* suspension 3. The Preparation of Drug Solution Taking appropriate amount of the above mentioned amphotericin B, mycostatin, natamycin and the polyene diester compounds prepared by examples 1-8 and 10-12, dissolving in a little dimethyl sulfoxide respectively, using pH7 phosphate buffer to dilute into solution which is equivalent to contain amphotericin B, mycostatin, natamycin 280 Units per milliliter, taking 1 ml and using pH7 phosphate buffer to quantitatively dilute into solution which is equivalent to contain amphotericin B 1.4 μg/ml and 2.8 μg/ml, and is equivalent to contain 5.6 μg/ml of mycostatin and natamycin.

In addition, preparing the solution according to the same method, adding 40% defibered sheep serum, using pH7 phosphate buffer to quantitatively dilute into unit solution which is equivalent to contain amphotericin B 1.4 μg/ml and 2.8 μg/ml, and is equivalent to contain 5.6 μg/ml of mycostatin and natamycin. Testing according to PHARMACOPOEIA OF THE PEOPLES REPUBLIC OF CHINA, second part, 2005 edition, appendix XIA The Antibiotics Microorganism Test.

4. Medium

Medium: Improved Martin Agar Medium, PHARMACOPOEIA OF THE PEOPLES REPUBLIC OF CHINA, second part, 2005 edition, appendix p 84.

Results:

See table 2. The results show that, for the amphotericin B diester derivatives, mycostatin diester derivatives and natamycin diester derivatives (prodrugs) both themselves (without sheep blood serum) and those after adding sheep blood serum, the diester derivatives all show similar anti-*Candida albicans*, anti-*Saccharomyces cerevisiae*, anti-*Candida mycoderma* activities to amphotericin B.

TABLE 2

The antibacterial activity in vitro of each polyene diester compound

| sample name | Concentration after conversion (μg/ml) | Whether add serum | Candida albicans 0 h | 6 h | 24 h | 48 h | Saccharomyces cerevisiae 0 h | 6 h | 24 h | 48 h | Candida mycoderma 0 h | 6 h | 24 h | 48 h |
|---|---|---|---|---|---|---|---|---|---|---|---|---|---|---|
| amphotericin B | 1.4 | No | ++ <br>+ | ++ <br>+ | ++ <br>+ | ++ <br>+ | ++ <br>++ | ++ <br>++ | ++ <br>++ | ++ <br>++ | ++ <br>+ | ++ <br>+ | ++ <br>+ | ++ <br>+ |
|  |  | Yes | ++ <br>+ | ++ <br>+ | ++ <br>+ | ++ <br>+ | ++ <br>++ | ++ <br>++ | ++ <br>++ | ++ <br>++ | ++ <br>+ | ++ <br>+ | ++ <br>+ | ++ <br>+ |
|  | 2.8 | No | ++ <br>++ | ++ <br>++ | ++ <br>++ | ++ <br>++ | ++ <br>++ <br>+ | ++ <br>++ <br>+ | ++ <br>++ <br>+ | ++ <br>++ <br>+ | ++ <br>++ | ++ <br>++ | ++ <br>++ | ++ <br>++ |
|  |  | Yes | ++ <br>++ | ++ <br>++ | ++ <br>++ | ++ <br>++ | ++ <br>++ <br>+ | ++ <br>++ <br>+ | ++ <br>++ <br>+ | ++ <br>++ <br>+ | ++ <br>++ | ++ <br>++ | ++ <br>++ | ++ <br>++ |
| amphotericin B methyl pivalate | 1.4 | No | + | + | + | + | + | + | + | + | + | + | + | + |
|  |  | Yes | + | ++ | ++ <br>+ | ++ <br>+ | + | ++ <br>+ | ++ <br>++ | ++ <br>++ | + | ++ | ++ <br>+ | ++ <br>+ |
|  | 2.8 | No | ++ | ++ | ++ | ++ | ++ | ++ | ++ | ++ | ++ | ++ | ++ | ++ |
|  |  | Yes | ++ | ++ <br>+ | ++ <br>++ | ++ <br>++ | ++ | ++ <br>+ | ++ <br>++ | ++ <br>++ <br>+ | ++ | ++ <br>+ | ++ <br>++ | ++ <br>++ |
| amphotericin B isopropoxycarbonyloxyethyl ester | 2.8 | No | ++ | ++ | ++ <br>+ | ++ <br>++ | + | + | + | + | ++ | ++ | ++ | ++ |
|  |  | Yes | ++ | ++ | ++ <br>+ | ++ <br>++ | ++ | ++ | ++ <br>+ | ++ <br>++ | ++ | ++ <br>+ | ++ <br>++ | ++ <br>++ |
| amphotericin B ethoxycarbonyloxyethyl ester | 2.8 | No | ++ <br>+ | ++ <br>+ | ++ <br>+ | ++ <br>+ | ++ | ++ | ++ | ++ | + | + | + | + |
|  |  | Yes | ++ <br>+ | ++ <br>++ | ++ <br>++ | ++ <br>++ | ++ | ++ <br>+ | ++ <br>++ | ++ <br>++ <br>+ | + | ++ <br>+ | ++ <br>+ | ++ <br>++ |
| amphotericin B cyclohexyloxycarbonyloxyethyl ester | 2.8 | No | + | + | + | + | ++ | ++ | ++ | ++ | ++ | ++ | ++ | ++ |
|  |  | Yes | + | ++ | ++ <br>+ | ++ <br>++ | ++ | ++ <br>+ | ++ <br>++ | ++ <br>++ <br>+ | ++ | ++ <br>+ | ++ <br>++ | ++ <br>++ |
| amphotericin B ethyl acetate | 2.8 | No | ++ <br>+ | ++ <br>+ | ++ <br>+ | ++ <br>+ | + | + | + | + | ++ | ++ | ++ | ++ |
|  |  | Yes | ++ <br>+ | ++ <br>++ | ++ <br>++ | ++ <br>++ | ++ | ++ <br>+ | ++ <br>++ | ++ <br>++ <br>+ | ++ | ++ <br>+ | ++ <br>++ | ++ <br>++ |
| amphotericin B-5-methyl-1,3-dioxol-2-one-4-methyl ester | 2.8 | No | ++ | ++ | ++ | ++ | ++ | ++ | ++ | ++ | ++ | ++ | ++ | ++ |
|  |  | Yes | ++ | ++ <br>+ | ++ <br>++ | ++ <br>++ | ++ | ++ <br>+ | ++ <br>++ | ++ <br>++ <br>+ | ++ | ++ <br>+ | ++ <br>++ | ++ <br>++ |
| amphotericin B-1,3-2H-3-oxo-1-ethyl benzofuran ester | 2.8 | No | + | + | + | + | ++ | ++ | ++ | ++ | ++ | ++ | ++ | ++ |
|  |  | Yes | + | ++ | ++ <br>+ | ++ <br>++ | ++ | ++ <br>+ | ++ <br>++ | ++ <br>++ <br>+ | ++ | ++ <br>+ | ++ <br>++ | ++ <br>++ |
| mycostatin | 5.6 | No | + | + | + | + | ++ <br>++ | ++ <br>++ | ++ <br>++ | ++ <br>++ | ++ <br>+ | ++ <br>+ | ++ <br>+ | ++ <br>+ |
|  |  | Yes | + | + | + | + | ++ <br>++ | ++ <br>++ | ++ <br>++ | ++ <br>++ | ++ <br>+ | ++ <br>+ | ++ <br>+ | ++ <br>+ |
| mycostatin methyl pivalate | 5.6 | No | + | + | + | + | ++ | ++ | ++ | ++ | ++ <br>+ | ++ <br>+ | ++ <br>+ | ++ <br>+ |
|  |  | Yes | + | + | + | + | + | ++ | ++ <br>+ | ++ <br>++ | + | ++ | ++ <br>+ | ++ <br>+ |
| mycostatin ethyl acetate | 5.6 | No | + | + | + | + | ++ | ++ | ++ | ++ | ++ | ++ | ++ | ++ |
|  |  | Yes | + | + | + | + | ++ | ++ | ++ <br>+ | ++ <br>++ | ++ | ++ | ++ <br>+ | ++ <br>+ |
| Natamycin | 5.6 | No | ++ | ++ | ++ | ++ | ++ <br>++ | ++ <br>++ | ++ <br>++ | ++ <br>++ | ++ <br>+ | ++ <br>+ | ++ <br>+ | ++ <br>+ |
|  |  | Yes | ++ | ++ | ++ | ++ | + <br>++ | + <br>++ | + <br>++ | + <br>++ | ++ <br>+ | ++ <br>+ | ++ <br>+ | ++ <br>+ |
| Natamycin methyl pivalate | 5.6 | No | + | + | + | + | + | + | + | + | ++ | ++ | ++ | ++ |
|  |  | Yes | + | ++ | ++ | ++ | + | ++ | ++ <br>+ | ++ <br>++ | ++ | ++ <br>+ | ++ <br>+ | ++ <br>+ |
| natamycin ethoxycarbonyloxyethyl ester | 5.6 | No | + | + | + | + | + | + | + | + | + | + | + | + |
|  |  | Yes | + | ++ | ++ | ++ | + | ++ | ++ <br>+ | ++ <br>++ | + | ++ | ++ <br>+ | ++ <br>+ |

Note:
The representation method of the diameter of the bacteria-inhibition zone: 16-18 mm: +++++, 14-16 mm: ++++, 12-14 mm: +++, 9-12 mm: ++, 7-9 mm: +

Test method: Double-plate counting method; us 5 ing bacteria bed 15 ml to replace the double layers, culture temperature: 37° C., time: 24 h; strain concentration: 1%
Medium: Modified Martin Broth Medium
Test organism:

EXAMPLE 25

Test of Esterase Hydroxylation In Vivo

Figure 2:
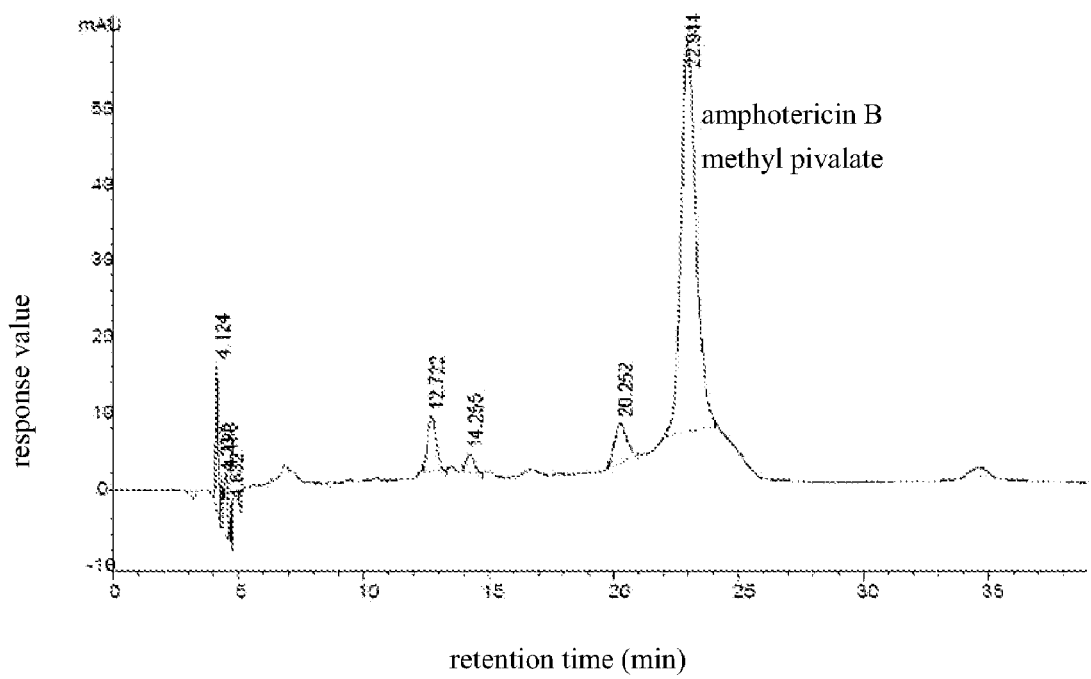
FIG. 2 shows the chromatogram of amphotericin B methyl pivalate prepared by example 1 under the HPLC test conditions according to this invention.
Figure 3:
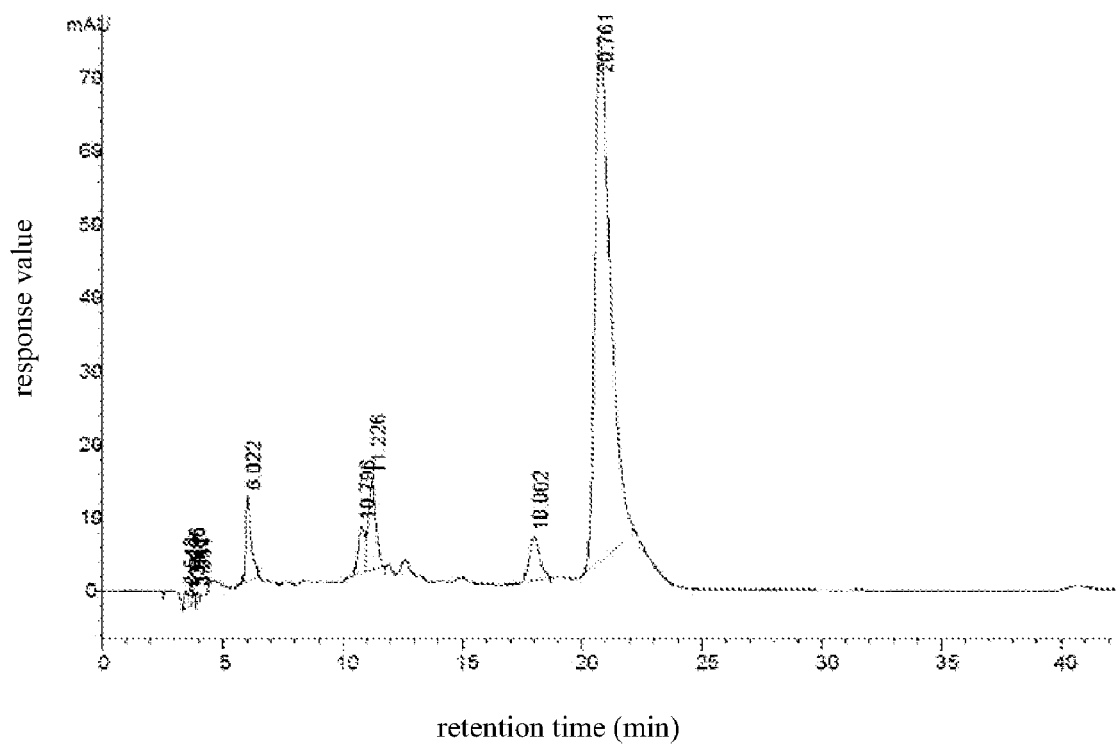
FIG. 3 shows the chromatogram of amphotericin B methyl pivalate prepared by example 1 cultured 2 hours after mixed with sheep blood serum at 37° C. under the HPLC test conditions according to this invention.
Figure 4:
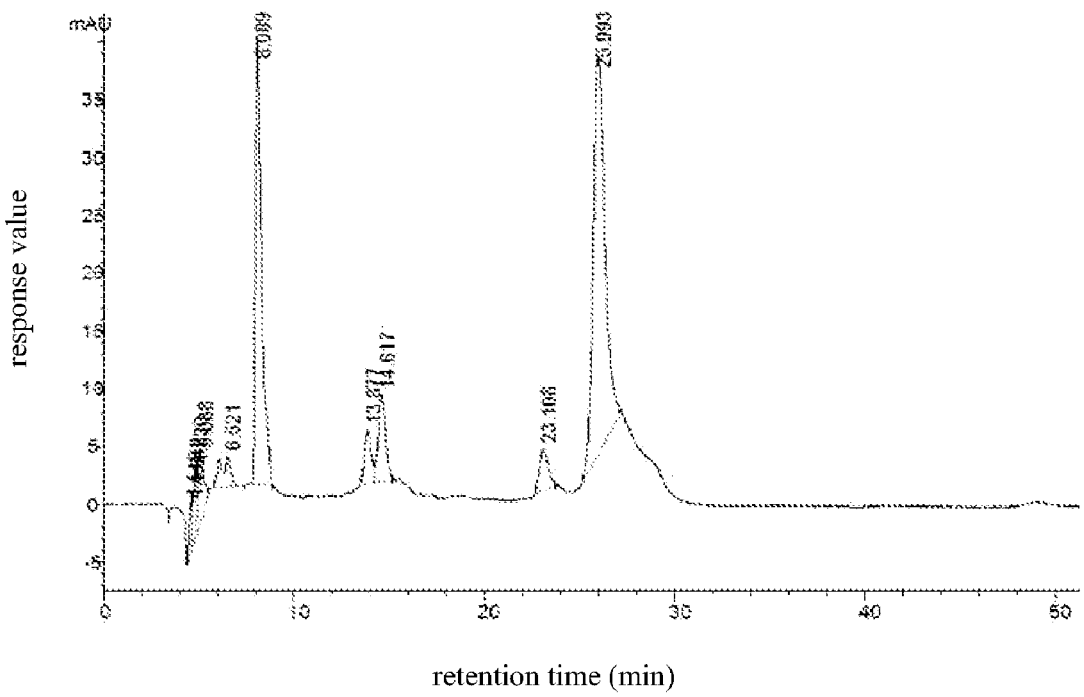
FIG. 4 shows the chromatogram of amphotericin B methyl pivalate prepared by example 1 cultured 6 hours after mixed with sheep blood serum at 37° C. under the HPLC test conditions according to this invention.
Figure 5:
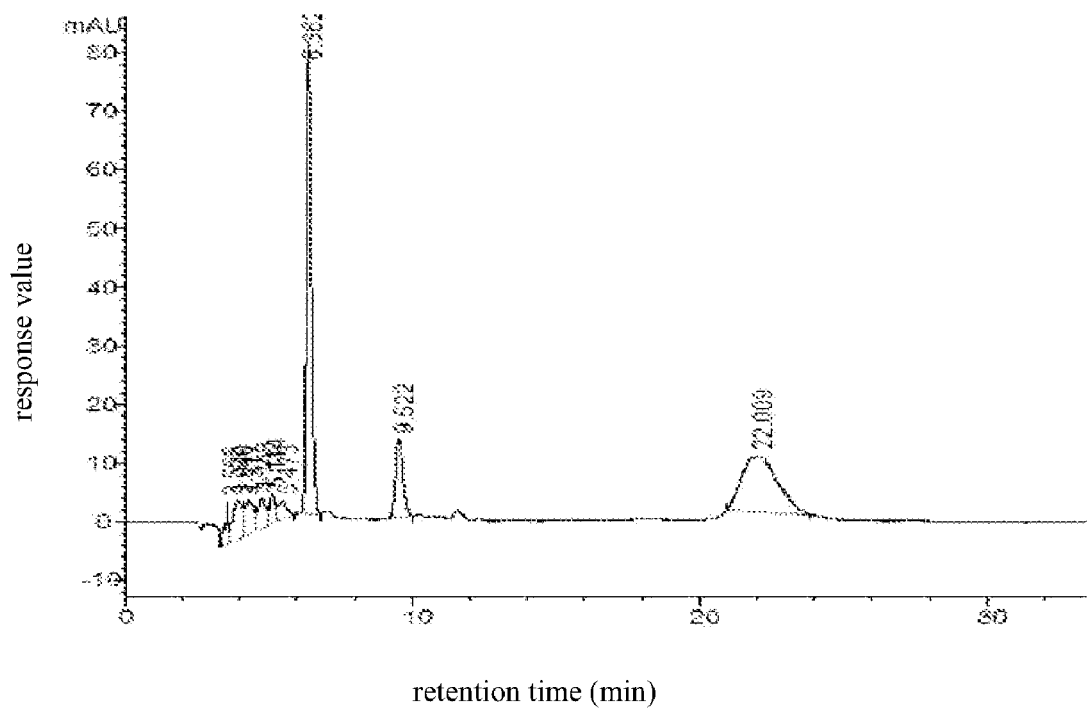
FIG. 5 shows the chromatogram of amphotericin B methyl pivalate prepared by example 1 cultured 24 hours after mixed with sheep blood serum at 37° C. under the HPLC test conditions according to this invention.

Materials and Methods:
1. Drugs
Experiment drugs: the amphotericin B methyl pivalate prepared by example 1
Control drug: amphotericin B (standard product)
2. The Test Conditions of the High Performance Liquid Chromatography (HPLC):
The stationary phase: Hypersil ODS2 5 um 4.6 mm×250 mm
The mobile phase: methanol: acetonitrile: EDTA-2Na (0.5 mmol)=60:20:20 flow rate: 1 ml/min
Detection system: ultraviolet detection, detection wavelength: 410 nm
3. The Preparation of Drug Solution
Taking appropriate amount of the above mentioned amphotericin B, and amphotericin B methyl pivalate prepared by example 1, dissolving in a little dimethyl sulfoxide respectively, using pH7 phosphate buffer to dilute into solution which is equivalent to contain amphotericin B 280 Units per milliliter, taking 1 ml and using pH7 phosphate buffer to quantitatively dilute into solution which is equivalent to contain amphotericin B 2.8 μg/ml.
Again, preparing the solution according to the same method, adding 10% defibered sheep blood serum, using pH7 phosphate buffer to quantitatively dilute into solution which is equivalent to contain amphotericin B 2.8 μg/ml.
4. Mixing the amphotericin B methyl pivalate prepared by example 1 with sheep blood serum at 37° C. and culturing.
Results: see FIGS. 1-5.
The results show that, under the effect of sheep blood serum cultivation at 37° C., the amphotericin B methyl pivalate is gradually hydrolyzed by esterase, and the original drug of amphotericin B is released.
24 hours after the amphotericin B methyl pivalate is add with 10% defibered sheep blood serum and cultured at 37° C., most of the diester derivative is hydrolyzed by esterase to release amphotericin B, by using amphotericin B to mix with the sample, it is proved that the hydrolyzed product is amphotericin B rather than other product.

EXAMPLES 26-31

Test of Esterase Hydroxylation In Vivo

Using the compounds prepared by examples 2-7 as experiment drugs and repeating example 25, and getting similar results.

EXAMPLES 32-34

Test of Esterase Hydroxylation In Vivo

Referring to the test conditions of HPLC of example 25, wherein the mobile phase is acetonitrile: 0.05M ammonium acetate solution=60:40.
Using mycostatin as control drug, and using the compounds prepared by examples 8-10 as experiment drugs and repeating example 25, and getting similar results.

EXAMPLES 35-36

Test of Esterase Hydroxylation In Vivo

Referring to the test conditions of HPLC of example 25, wherein the mobile phase is acetonitrile: 0.05M ammonium acetate solution=60:40.
Using natamycin as control drug, and using the compounds prepared by examples 11-12 as experiment drugs and repeating example 25, and getting similar results.

EXAMPLE 37

Prepare the Tablet of Amphotericin Methyl Pivalate

|  | content (mg) |
| --- | --- |
| Amphotericin methyl pivalate | 50 |
| lactose | 3 |
| microcrystalline cellulose | 5 |
| starch | 142 |
| magnesium stearate | appropriate amount |

Preparing the tablet of amphotericin methyl pivalate according to the above formulation.

All the documents referred in this invention are incorporated herein as reference, the same as if every document is solely cited as reference. Besides, it should be understood that, after reading the content taught above by this invention, those skilled in the art may make various changes or amendments to this invention, and these equivalent varieties also fall into the scope defined by the attached claims of the invention.

The invention claimed is:
1. A polyene diester compound represented by Formula 1 or pharmaceutically available salt thereof:

PA-COOR        Formula 1 wherein, PA is selected from the following polyene antibiotic nuclear parent compounds:

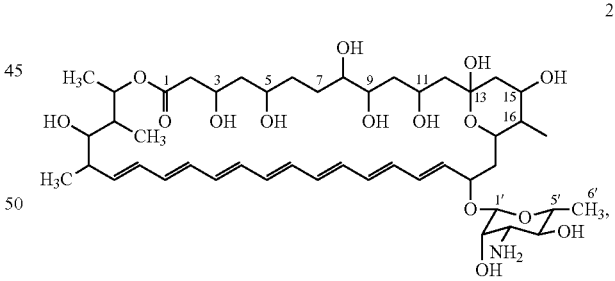

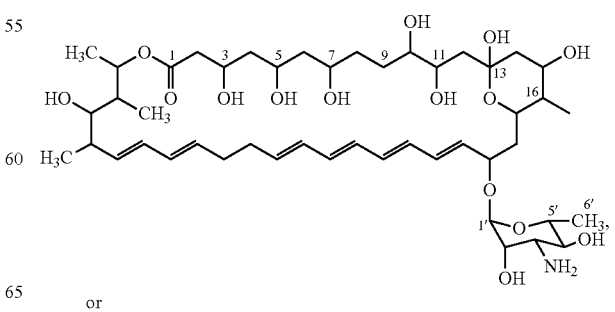

or

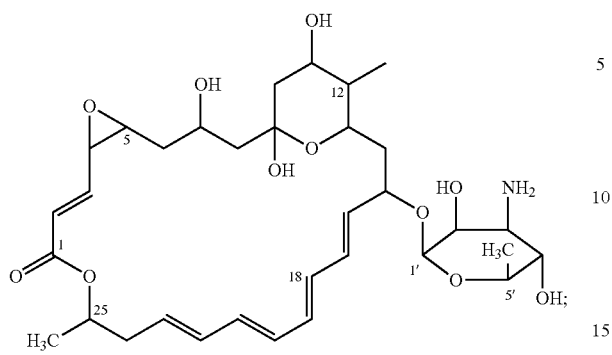
R is a linear or cyclic carbonate or a carboxylic acid ester group.
2. The compound of claim 1, or pharmaceutically available salt thereof, wherein said PA has the following stereostructure:
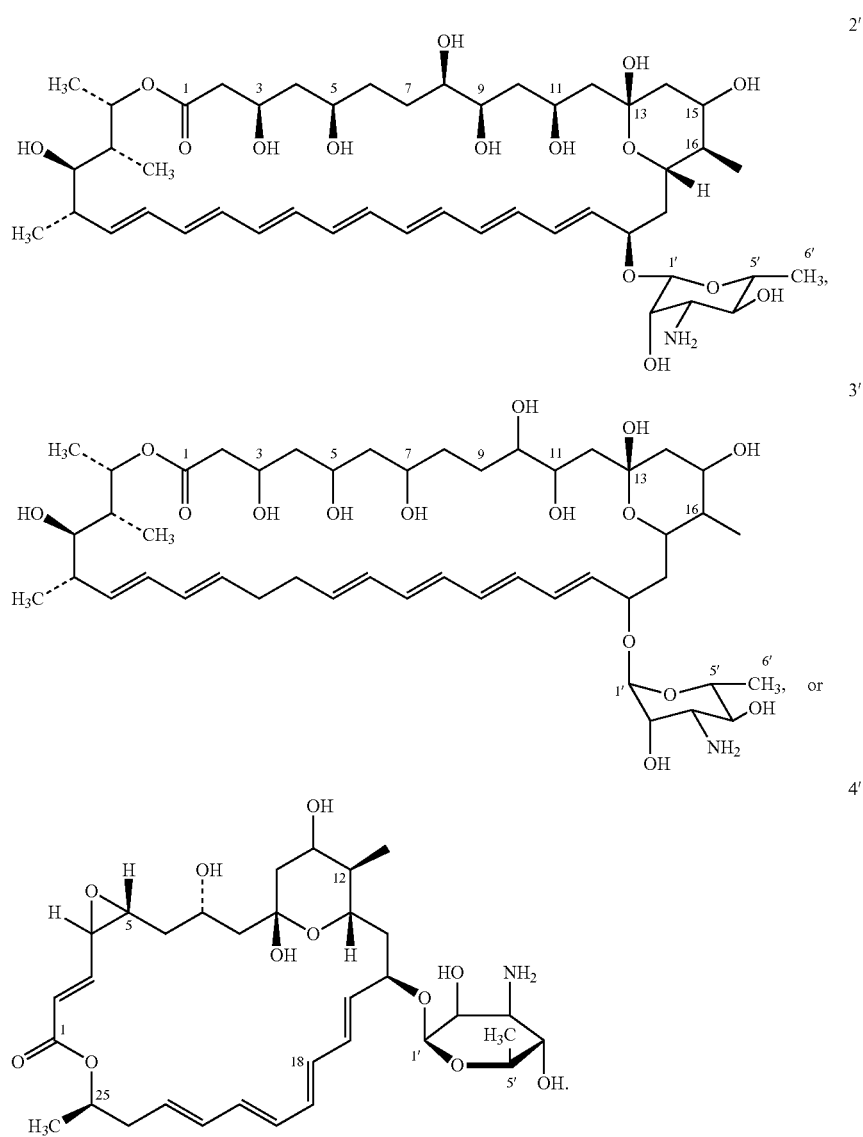

3. The compound of claim 1 or 2, wherein R is a group containing 2-15 carbon atoms and having 1-3 linear or cyclic carbonate or carboxylic acid ester groups.

4. The compound of claim 3, wherein R is selected from:

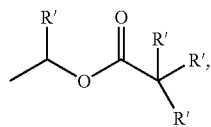  5

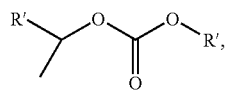  18

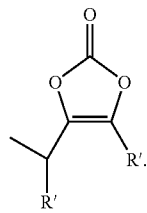  19

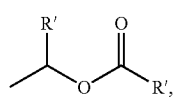  20

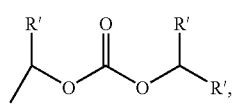  21

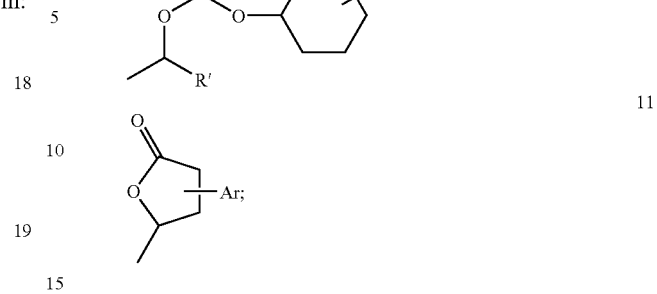

wherein, R' is selected from halogen, C1-C3 alkyl or hydroxyl;

Ar is selected from an aryl group; hetero aromatic rings containing nitrogen, sulphur, oxygen; or, substituted aryl or substituted hetero aromatic rings containing nitrogen, sulphur, oxygen with 1-3 substituents selected from a halogen, a C1-C3 alkyl group, an amino group or a hydroxyl group.

5. The compound of claim 4, wherein said Ar is benzene or a substituted benzene, and said substituent is selected from a halogen, a C1-C3 alkyl group, an amino group, or a hydroxyl group.

6. A method for preparing the compound of claim 1, the method comprising the steps of:

(a) reacting a polyene antibiotic or its salt with a halogen-containing ester compound in an organic solvent to produce a reaction mixture containing the polyene diester compound represented by Formula 1:

PA-COON+RX→PA-COOR    (Formula 1)

wherein, PA is selected from the following polyene antibiotic nuclear parent compounds:

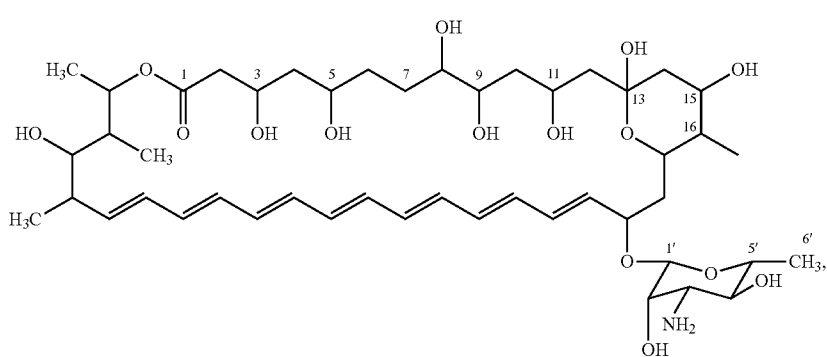

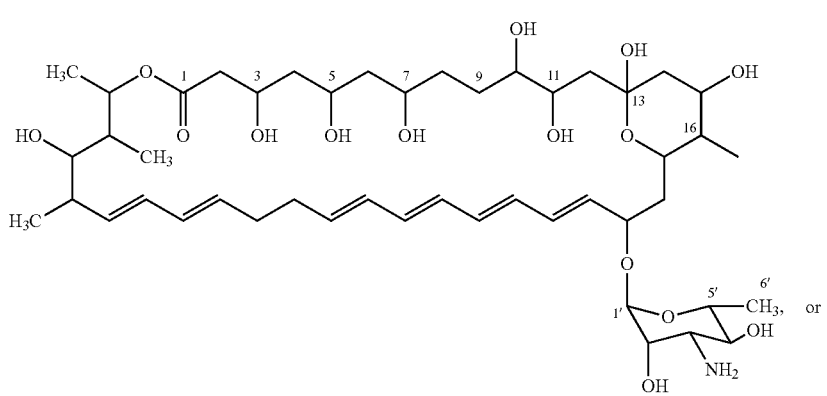

-continued

4

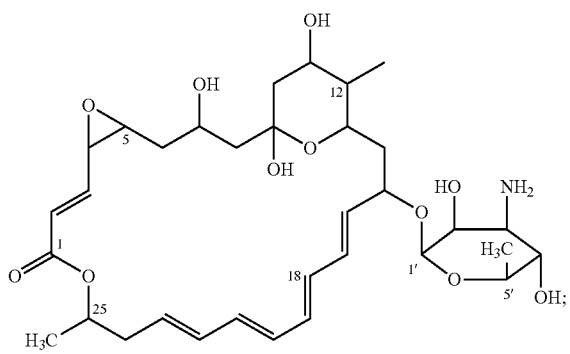

wherein, R is a linear or cyclic carbonate or a carboxylic acid ester group; and X is Cl, Br, or I;

(b) separating the polyene diester compound represented by Formula 1 from the reaction mixture.

7. The method according to claim 6, wherein R is selected from:

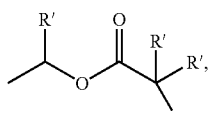
18

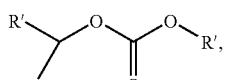
19

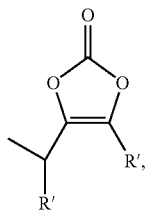
20

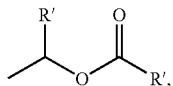
21

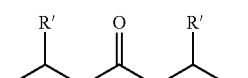
22

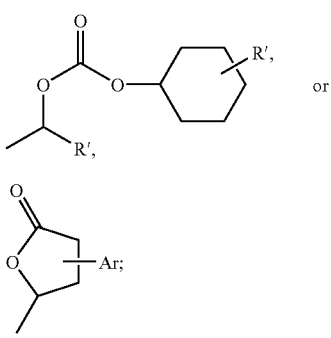
23 or

11 wherein, R' is selected from a halogen, a C-C3 alkyl group or a hydroxyl group;

Ar is selected from an aryl group; hetero aromatic rings containing nitrogen, sulphur, oxygen; or, substituted aryl or substituted hetero aromatic rings containing nitrogen, sulphur, oxygen with 1-3 substituents selected from a halogen, a C1-C3 alkyl group, an amino ammo group or a hydroxyl group.

8. The method according to claim 6, wherein in step (a), the polyene antibiotic, or its salt, and halogen-containing ester compound are reacted in an aprotic solvent.

9. A pharmaceutical composition, comprising a therapeutically effective amount of the compound of claim 1 and a pharmaceutically acceptable carrier.

10. The compound of claim 1 for use in an antifungal treatment or an anti-HIV treatment.

11. A method for preparing a pharmaceutical composition, characterized in that said method includes the steps of: mixing the compound of claim 1 with a pharmaceutically acceptable carrier to form the pharmaceutical composition.

\* \* \* \* \*